United States Patent [19]

Cartmell et al.

[11] Patent Number: 4,710,175
[45] Date of Patent: Dec. 1, 1987

[54] INTRAVENOUS INFUSION ASSEMBLY FORMED AS AN INTEGRAL PART

[75] Inventors: Robert L. Cartmell, Kettering; Charles W. Daugherty, Xenia; David B. Ireland, Dayton, all of Ohio

[73] Assignee: Deseret Medical, Inc., Franklin Lakes, N.J.

[21] Appl. No.: 829,457

[22] Filed: Feb. 12, 1986

Related U.S. Application Data

[63] Continuation of Ser. No. 524,728, Aug. 19, 1983, abandoned.

[51] Int. Cl.⁴ .................................................. A61M 5/00
[52] U.S. Cl. ........................................ 604/177; 604/283
[58] Field of Search ......................... 604/177, 164–170, 604/283; 156/580.1

[56] References Cited

U.S. PATENT DOCUMENTS

| | | | |
|---|---|---|---|
| 3,670,727 | 6/1972 | Reiterman | 604/177 |
| 3,966,520 | 6/1976 | Fallenbeck et al. | 156/580.1 |
| 4,217,895 | 8/1980 | Sagae et al. | 604/167 |
| 4,314,555 | 1/1982 | Sagae | 604/167 |
| 4,389,210 | 6/1983 | Genese | 604/177 |

Primary Examiner—Dalton L. Truluck
Attorney, Agent, or Firm—Robert P. Grindle

[57] ABSTRACT

An integral polyurethane winged catheter assembly formed by RF heating individual catheter parts is disclosed.

1 Claim, 6 Drawing Figures

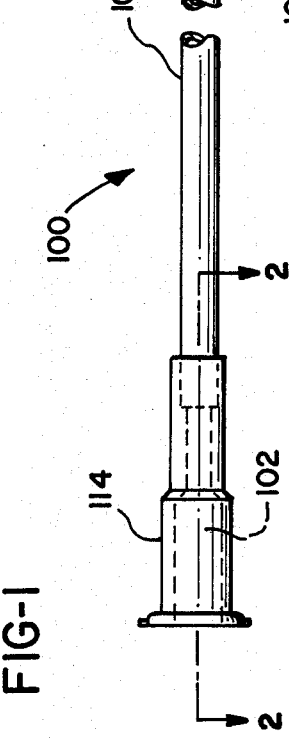
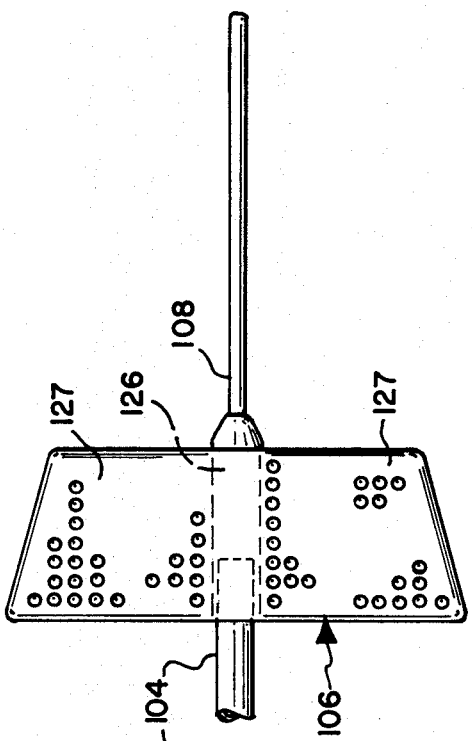
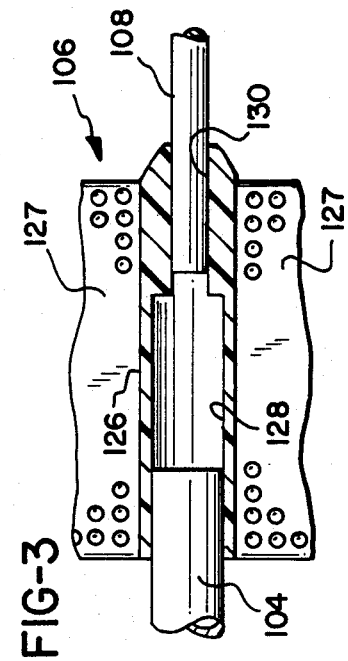

INTRAVENOUS INFUSION ASSEMBLY FORMED AS AN INTEGRAL PART

This is a continuation of co-pending application Ser. No. 524,728 filed on Aug. 19, 1983 abandoned.

BACKGROUND OF THE INVENTION

This invention relates generally to intravenous infusion and, more particularly, to a winged catheter for intravenous infusion which is assembled from a plurality of polyurethane parts and formed into an integral unit by means of dielectric heating using radio frequency energy.

Commonly used intravenous infusion assemblies comprise needle and catheter sets wherein a needle extends within a flexible catheter having so-called "wings" attached to the catheter assembly. For insertion, one grips the wings, squeezing them between the thumb and forefinger, to assist in accurately positioning the catheter sheathed needle into a desired vein.

Once positioned, the needle is removed from the catheter leaving only the flexible catheter in place such that the vein is not likely to be ruptured as a result of minor relative movements between the infusion assembly and the vein. Two varieties of combination needle/catheter sets are shown respectively in U.S. Pat. No. 3,094,122 issued Jan. 18, 1963 to Gauthier et al. and U.S. Pat. No. 4,362,156 issued Dec. 7, 1982 to Feller et al.

It is important that the individual elements forming the infusion assembly be securely bonded together to prevent leakage from the assembly and detachment of the catheter. Many of the solutions passed through an intravenous infusion assembly may cause discomfort or pain if allowed to contact a patient's skin. This is particularly true with many chemotherapuptic agents utilized to treat cancer patients. Even if the solution is not toxic, bacterial contamination is a problem once an opening appears in the intravenous infusion assembly. The complications of a detached catheter within a patient's vein are potentially even graver. Accordingly, serious problems can arise if the catheter assembly is not properly manufactured.

A typical infusion assembly comprises a catheter, a winged catheter gripping member, a section of tubing and a fluid receiving hub. In the prior art, a variety of methods have been utilized to interconnect the parts making up such an assembly. The parts have been mechanically interconnected by forcing a conical wedge into the proximal end of the catheter to lock the catheter in the catheter hub. Such mechanical interconnection is often referred to as "staking" or "swedging" and can be expensive and time consuming. Futhermore, the presence of the wedge in the infusion stream creates turbulent flow which can interfere with metering the infusion liquid.

The parts have also been glued together by means of an appropriate adhesive. However, gluing requires a biocompatible adhesive and is typically messy. Gluing also can lead to inadvertent blockage of a portion of the assembly passageway particularly when small gauge catheters are utilized.

Solvent bonding has also been utilized. In solvent bonding, each of the parts is made from a material which is soluble in a particular solvent. When the solvent is applied to the parts and the parts are intermated, dissolved surface portions of the two intermingle with one another to form a bond. Unfortunately, solvent bonding has proved to be only marginally reliable in preventing leakage. Solvent bonding also is expensive and time consuming when used for the assembly of intravenous infusion devices.

One assembly means which has been used in forming a Foley catheter unit is by welding the individual parts together using dielectric heating cuased by radio frequency (RF) energy. However, radio frequency welding or bonding has not been applied in the manufacture of intravenous infusion assemblies. Problems encountered in RF bonding have centered around the frequencies and power levels utilized as well as the formation of the power applying electrodes. For example, if insufficient power is applied to the parts, the welds or bonds are not reliable. On the other hand, excessive power can lead to arcing of the radio frequency energy at the electrodes and may damage the RF power supply and/or cause the small openings of the passageways through the intravenous infusion assembly to be blocked.

Thus, it is apparent that the need exists for an integral catheter intravenous infusion assembly which will provide high reliability against leakage of possibly toxic materials onto a patient's skin as well as detachment of the catheter from the intravenous infusion assembly.

SUMMARY OF THE INVENTION

In accordance with the present invention, a winged catheter assembly for intravenous infusion is formed as an integral unit from a plurality of polyurethane parts by means of welding the parts together using dielectric heating created by radio frequency energy. It has been found that catheter assemblies bonded by radio frequency heating in accordance with the present invention are particularly advantageous because the assembly can be manufactured from parts made from polyurethanes having the same or different shore hardness ratings and yet these parts can be integrally bonded together such that there is intermingling of their constituent polymers and they cannot be separated.

In accordance with the present invention, a section of flexible polyurethane tubing is inserted into a polyurethane fluid receiving hub and radio frequency energy is applied to the portion of the hub into which the tubing is inserted to heat the tubing and the hub such that they melt into one another to form a reliable weld or bond. Preferably, the fluid receiving hub includes tubing stop means, for example, an internal shoulder sized to engage the end of the tubing, for defining a tubing insertion point beyond which the tubing cannot be inserted into the hub.

The opposite end of the tubing section is inserted into a generally cylindrical central portion of a polyurethane winged catheter gripping member and radio frequency energy is again applied to weld the two together as if the two were a single part. The catheter gripping member includes a pair of wings flexibly connected to the central portion and having a relaxed condition wherein the wings extend in a generally transverse direction to the central portion, yet the wings are sufficiently flexible that they can be moved into facing engagement with one another for placement of the catheter into a selected vein. Finally, a generally cylindrical polyurethane catheter has it proximal end inserted into a canal in the generally cylindrical central portion of the catheter gripping member and is welded to it by the application of radio frequency energy with the catheter having its tapered distal end extending from the gripping member for insertion into a vein.

Such assembly and welding operations using radio frequency energy provide a winged catheter assembly which is an integral unit, i.e., the individual elements forming the infusion assembly are so bonded to one another that the polymers at the interface of two adjacent parts are intermingled.

A process for making an integral polyurethane winged catheter assembly for intravenous infusion including a fluid receiving hub, a winged catheter gripping member, tubing for interconnecting the hub to the gripping member, and a catheter, all of which are formed from polyurethane compounds, comprises the steps of interconnecting the individual parts together and applying the appropriate frequency and energy levels of RF energy to the sections of the parts receiving the tubing and the catheter such that the polyurethane compounds of the energized portions of the parts are heated to flow into one another to form an integral winged catheter assembly.

It is, therefore, an object of the present invention to provide an improved intravenous infusion assembly which is formed as an integral unit from a plurality of parts made from polyurethane compounds of the same or different hardness with the individual parts being assembled and welded to form an integral unit by means of the application of the appropriate frequency and energy levels of radio frequency energy to interengaging portions of the assembly to thereby fuse the interengaging portions of the respective parts and firmly weld them to one another.

Other objects and advantages of the invention will be apparent from the following description, the accompanying drawings and the appended claims.

BRIEF DESCRIPTION OF THE DRAWINGS

FIG. 1 is a plan view of an intravenous infusion assembly in accordance with the present invention.

FIG. 2 is a sectional view of the fluid infusion hub of FIG. 1 taken along the line 2—2.

FIG. 3 is a sectional view of the central portion of the catheter gripping member of FIG. 1 taken along the line 3—3.

DETAILED DESCRIPTION OF THE INVENTION

Figure 4:
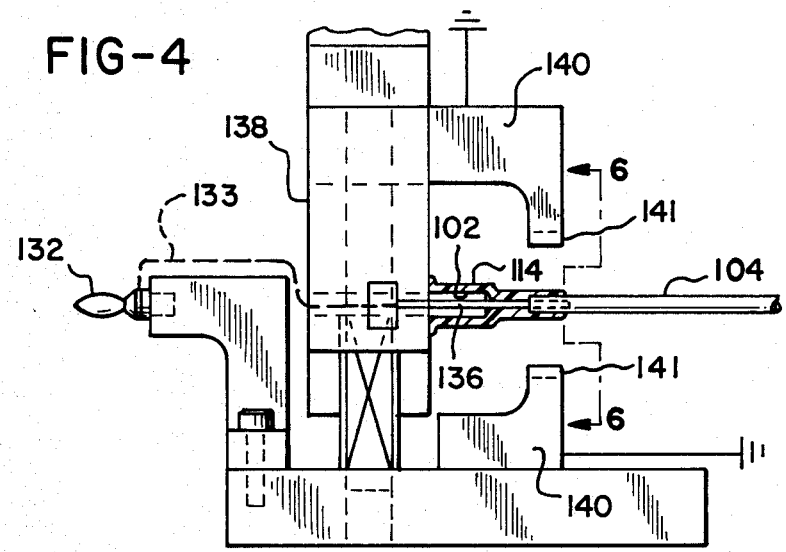
FIG. 4 is a side view of apparatus for engaging a fluid infusion hub and applying radio frequency energy to a section of that hub into which a section of tubing has been inserted.

In FIG. 1, an intravenous infusion assembly 100 in accordance with the present invention comprises a fluid receiving hub 102, a section of flexible tubing 104, a winged catheter gripping member 106 and a catheter 108 all formed into an integral unit by means of radio frequency welding or bonding as will be described hereinafter.

The fluid receiving hub 102, shown in cross-section in FIG. 2, comprises a hollow, generally cylindrical, body molded from a relatively rigid polyurethane compound. Typically, the polyurethane forming the hub has a Shore Durometer D hardness of about 50 to 75 and the polyurethane forming the tubing has a Shore Durometer A of about 75 to 95.

The proximal end of the hub 102 has a collar 110 with radially and circumferentially extending lugs 112 that may be used with conventional equipment employing Luer locks for external connection to a source of infusion fluid. Reinforcing ribs 114 run approximately two-thirds of the way along the hub from the collar 110 toward the distal end of the hub.

The hub 102 comprises a primary fluid receiving cavity 116 opening to its proximal end and a tubing receiving canal 118 opening to the distal end of the hub 102. The primary fluid receiving cavity 116 and the tubing receiving canal 118 are interconnected by a diameter reducing frustoconical section 120 and a generally cylindrical interconnecting canal 122 which is of a smaller diameter than the diameter of the generally cylindrical tubing receiving canal 118. The reduced diameter canal 122 forms a tubing stop means or shoulder 124 such that when the tubing 104 is inserted into the tubing receiving canal 118, it is extended only until it engages the shoulder 124 to provide a selected or defined length of the tubing 104 extending into the hub 102.

As shown in FIG. 1, the winged catheter gripping member 106 comprises a generally cylindrical central portion 126 to which the wings 127 are flexibly connected. The gripping member is preferably formed from a relatively soft polyurethane e.g., one having a Shore Durometer A hardness of about 75 to 90 such that the wings 127, as shown in FIG. 1, can be folded upwardly into facing engagement with one another and be firmly gripped between the thumb and forefinger of a person inserting the catheter assembly into a vein of a patient. A cannula or needle (not shown) is included within the catheter assembly 100 for insertion of the catheter 108 into a vein as is well known in the art.

The generally cylindrical central portion 126 of the member 106, shown in cross-section in FIG. 3, includes a first opening 128 toward its proximal end sized to frictionally receive the distal end of the tubing 104. The exact insertion depth of the tubing 104 into the opening 128 is not critical. It is only necessary that the tubing 104 extend a sufficient distance into the passageway 128 such that it may be securely welded by means of dielectric heating generated by RF energy applied to the central portion 126 as will be described hereinafter.

The distal end of the central portion 126 includes a downsized opening 130 which is sized to receive the proximal end of the catheter 108. The catheter 108 may be inserted a varying depth into the opening 130 and, again, the only requirement is that a sufficient insertion depth be made such that the catheter 108 and the surrounding portion of the central section 128 forming the opening 130 may be firmly welded to one another by means of dielectric heating. A particular advantage of the present invention is that an integral catheter assembly can be formed from polyurethane elements without unduly restricting the nature of the polyurethane which forms the catheter. Thus, the catheter can be formed from a polyurethane which is hard enough to be inserted through the skin on a cannula but is sufficiently pliable as to not scratch or damage the inside wall of a vein or artery into which the catheter is inserted. Polyurethanes used for this purpose usually have a Shore Durometer D hardness of about 55 to 70.

Figure 5:
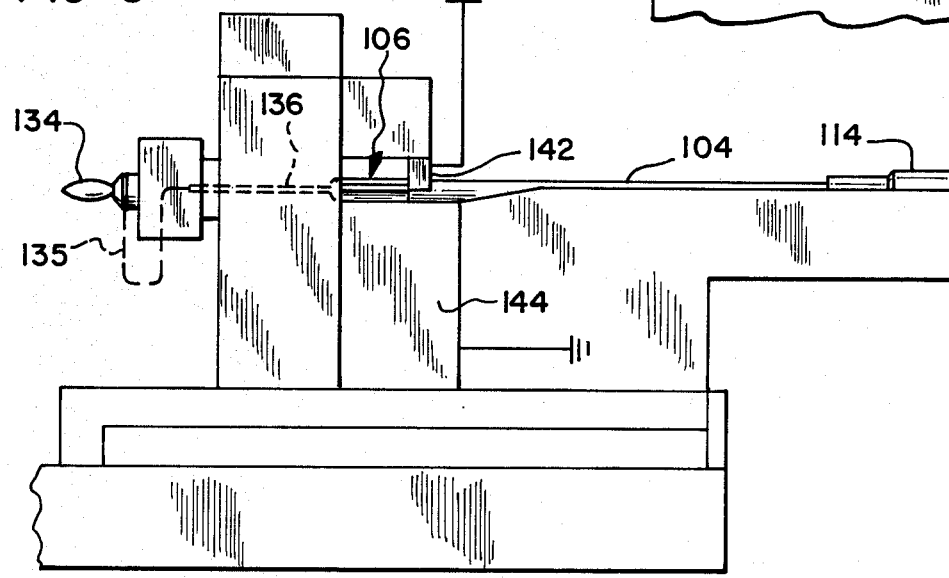
FIG. 5 is a side view of apparatus for applying radio frequency energy to a winged catheter gripping member to thereby weld the member to polyurethane tubing inserted into one end.

FIG. 4 shows a jig for welding the tubing 104 to the hub 102 and FIG. 5 shows a jig for welding the tubing 104 into the central portion 126 of the winged catheter gripping member 106. RF energy from a Solidyne KH 8 RF generator from Solidyne, Inc. (not shown) is connected to terminal lugs 132 and 134 of the jigs shown in FIGS. 4 and 5, respectively which in turn are connected to a metal pin 136 on which the catheter assembly is mounted as it is welded. An alternating current is delivered to the pin 136 by the generator which causes the polarity of the pin to rapidly oscillate between a highly positive and a highly negative polarity with respect to ground. Thus, an alternating electric field is set up between the pin 136 and the electrodes 140 which are grounded.

Because it is difficult to maintain uniform voltage distribution over large areas and a relatively small bond area is sufficient to form the assembly into an integral unit, electrodes 140 are designed with smaller dimension tips 141 where the field is concentrated. The portions of the catheter assembly in the alternating field between the electrode tips 141 heat in a known manner. It is not essential that there be a space between the catheter assembly 100 and the ground electrodes 140 to prevent arcing. Sharp points and edges should be avoided in the electrodes wherever possible since these are the first places breakdown occurs.

Figure 6:
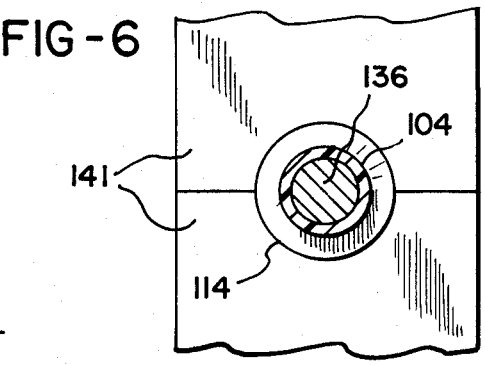
FIG. 6 shows an end view of electrodes for conducting radio frequency energy to the fluid infusion hub and tubing combination.

For welding the tubing 104 to the hub 102, a generally cylindrical pin 136 extends from the framework 138 of the jig shown in FIG. 4 with the generally cylindrical pin 136 being connected to the RF generator. The ground electrodes 141, an end view of which is shown in FIG. 6, are closed to engage one another and form an intimate contact from the forward portion of the hub 102 into which the tubing 104 has been inserted.

Bonding conditions will vary depending on the characteristics of the specific polyurethanes used, the electrode construction and the surroundings. The maximum voltage that can be used is limited by the voltage breakdown characteristics.

As a general rule, the frequency should be as high as possible so that the lowest voltage can be employed. However, at higher frequencies the equipment is more costly, it is difficult to deliver the power to the material as efficiently and it is more difficult to maintain uniform voltage distribution.

It has been found that RF energy at 1 to 100 mHz, preferably 25 to 70 mHz and most preferably 55 to 65 mHz is preferred for bonding the polyurethane parts of the winged catheter assembly of the present invention. However, there may be small changes in the preferred frequency as the polyurethane compositions change.

For bonding, the RF energy is connected at a power level of about 10 to 5,000 watts for a period of approximately 0.1 to 60 seconds preferably 100 to 300 watts for 2 to 11 seconds and actually at 200 watts for 4 seconds. It should be understood that the period can vary from 3 to 7 seconds depending upon the specific composition of the polyurethane compounds making up the tubing 104 and the hub 102 as well as the specific size and thickness of the hub and tubing.

The RF field is maintained for a period sufficient to melt the parts of the assembly only in the vicinity of the desired bond such that the polyurethanes forming the individual elements mingle but without loosing their form or blocking the channel through the assembly. The use of the electrode pin 136 makes the upper limits of the RF power applied to weld the tubing 104 to the hub 102 somewhat less restrictive since the member 136 maintains the opening into the tubing 104 in spite of marginal excesses of heating generated by the RF energy passing through the polyurethane materials.

FIG. 5 illustrates bonding tubing 104 into the central portion of the gripping member 106. There, the ground electrode 142 is lowered to engage the central cylindrical portion 126 of the winged catheter gripping assembly 106 at the location where the tubing 104 has been inserted into the member 106. RF energy is then applied through the terminal 134 via wire 135 to pin 136 with ground being applied to the base 144 of the jig and electrode 142 such that radio frequency energy passes through the gripping member 106 and the tubing 104.

It is critical that a power level be used which forms the objective integral bond without blocking the catheter. In the case of small gauge catheters, this is especially critical and the following power levels at a frequency of 63 mHz have been found to provide a reliably secure weld of the catheter to the cylindrical member 126 without providing blockage of the small opening of the catheter.

| Catheter Gauge | Power Level ± 15% at 5 secs |
|---|---|
| 16 | 200 watts |
| 18 | 200 watts |
| 20 | 200 watts |
| 22 | 200 watts |
| 24 | 200 watts |

While the process and product herein described constitute preferred embodiments of the invention, it is to be understood that the invention is not limited to this precise process and product and that changes may be made therein without departing from the scope of the invention which is defined in the appended claims.

What is claimed is:

1. A unitary winged catheter assembly comprised entirely of a plurality of polyurethane parts of varying degrees of hardness, said parts being dielectrically welded together into said unitary assembly, characterized by
   (a) a fluid receiving hub for said assembly;
   (b) said hub having a fluid receiving first end and a second end;
   (c) said hub being comprised of a substantially hard rigid polyurethane material having a Shore D hardness within the range of between about 50 and 75;
   (d) a fluid canal in said hub, said canal extending from said first end to said second end;
   (e) said canal having a reduced diameter portion adjacent said second end to define a tubing stop in said hub canal;
   (f) a length of substantially soft flexible polyurethane tubing having a Shore A hardness within the range of between about 75 and 95, said tubing having a first end and a second end;
   (g) the first end of said tubing extending into said second end of said hub to said tubing stop and forming a first joint for said assembly;
   (h) said first end of said tubing and said second end of said hub having internal diameters substantially equal at said tubing stop;
   (i) a gripping member comprised of a substantially soft flexible polyurethane having a Shore A hardness within the range of between about 75 and 90, and having a passageway extending therethrough from a first end of said gripping member to a second end thereof;

(j) the internal diameter of said gripping member passageway receiving in the first end thereof the said second end of said tubing, and forming a second joint for said assembly;

(k) a pair of substantially soft flexible polyurethane wings having a Shore A hardness within the range of between about 75 and 90 and positioned on said gripping member, and movable from a first position transverse to the axis of said passageway through said gripping member to a second position with said wings in facing relation to each other;

(l) a substantially rigid polyurethane catheter having a Shore D hardness within the range of between about 55 and 70 with a first end and a second end, and having the second end tapered for insertion into a vein;

(m) the first end of said catheter being inserted into the said second end of said passageway of said gripping member to form a third joint for said assembly;

(n) the internal diameter of said gripping member passageway being large enough to receive in the second end thereof the said first end of said catheter for said third joint;

(o) the mating surfaces of said first, second and third joints being joined together by dielectric welding for comingling the components of said mating surfaces; and (p) the internal diameters of said first, second and third joints being of sufficient diameter for receiving a dielectric electrode for said dielectric welding.

* * * * *